(12) United States Patent
Zalevsky

(10) Patent No.: US 7,061,693 B2
(45) Date of Patent: Jun. 13, 2006

(54) OPTICAL METHOD AND SYSTEM FOR EXTENDED DEPTH OF FOCUS

(75) Inventor: Zeev Zalevsky, Rosh HaAyin (IL)

(73) Assignee: Xceed Imaging Ltd., Rosh Haayin (IL)

( * ) Notice: Subject to any disclaimer, the term of this patent is extended or adjusted under 35 U.S.C. 154(b) by 52 days.

(21) Appl. No.: 10/974,943

(22) Filed: Oct. 28, 2004

(65) Prior Publication Data
US 2006/0034003 A1 Feb. 16, 2006

Related U.S. Application Data

(60) Provisional application No. 60/601,638, filed on Aug. 16, 2004.

(51) Int. Cl.
*G02B 9/00* (2006.01)
*G02B 27/46* (2006.01)

(52) U.S. Cl. .............. 359/738; 359/739; 359/559

(58) Field of Classification Search ............ 359/738, 359/739, 559, 558, 721, 740; 438/468, 535, 438/508
See application file for complete search history.

(56) References Cited

U.S. PATENT DOCUMENTS

| | | |
|---|---|---|
| 3,549,240 A | 12/1970 | Sawatari et al. |
| 4,955,904 A | 9/1990 | Atebara et al. .......... 623/6.17 |
| 5,225,858 A | 7/1993 | Portney .................. 351/161 |
| 5,245,387 A | 9/1993 | Kubo et al. .............. 351/161 |
| 5,260,727 A | 11/1993 | Oksman et al. |
| 5,302,477 A | 4/1994 | Dao et al. |
| 5,662,706 A | 9/1997 | Legerton et al. ......... 623/5.13 |
| 5,715,031 A | 2/1998 | Roffman et al. ......... 351/161 |
| 5,748,371 A | 5/1998 | Cathey, Jr. et al. ....... 359/558 |
| 5,757,458 A | 5/1998 | Miller et al. ............. 351/162 |
| 5,768,031 A | 6/1998 | Yang |
| 5,788,883 A | 8/1998 | Srivastava et al. ....... 351/162 |
| 5,905,561 A | 5/1999 | Lee et al. ................ 623/6.31 |
| 5,965,330 A | 10/1999 | Evans et al. ............. 430/321 |
| 5,980,040 A | 11/1999 | Xu et al. ................. 351/162 |

(Continued)

FOREIGN PATENT DOCUMENTS

EP  0 389 581  5/1990

(Continued)

OTHER PUBLICATIONS

Bradburn, S. et al; "Realizations of focus invariance in optical-digital systems with wave-front coding"; *Applied Optics, OSA, Optical Society of America*, vol. 36, No. 35, 1997, pp. 9157-9166.

(Continued)

*Primary Examiner*—Timothy Thompson
(74) *Attorney, Agent, or Firm*—Browdy and Neimark, PLLC

(57) ABSTRACT

An imaging arrangement and method for extended the depth of focus are provided. The imaging arrangement comprises an imaging lens having a certain affective aperture, and an optical element associated with said imaging lens. The optical element is configured as a phase-affecting, non-diffractive optical element defining a spatially low frequency phase transition. The optical element and the imaging lens define a predetermined pattern formed by spaced-apart substantially optically transparent features of different optical properties. Position of at least one phase transition region of the optical element within the imaging lens plane is determined by at least a dimension of said affective aperture.

45 Claims, 10 Drawing Sheets

U.S. PATENT DOCUMENTS

| | | | |
|---|---|---|---|
| 6,024,447 A | 2/2000 | Portney | 623/6.32 |
| 6,069,738 A | 5/2000 | Cathey, Jr. et al. | 359/550 |
| 6,097,858 A | 8/2000 | Laor | 382/312 |
| 6,172,957 B1 | 1/2001 | Ogasawara | |
| 6,451,058 B1 | 9/2002 | Tuke et al. | 623/6.18 |
| 6,474,814 B1 | 11/2002 | Griffin | 351/161 |
| 6,527,389 B1 | 3/2003 | Portney | 351/161 |
| 6,533,418 B1 | 3/2003 | Izumitani et al. | 351/160 R |
| 6,537,317 B1 | 3/2003 | Steinert et al. | 623/6.24 |
| 6,554,424 B1 | 4/2003 | Miller et al. | 351/160 R |
| 6,554,859 B1 | 4/2003 | Lang et al. | 623/6.28 |
| 6,576,012 B1 | 6/2003 | Lang | 623/6.28 |
| 2003/0142268 A1 | 7/2003 | Miller et al. | 351/165 |
| 2004/0114102 A1 | 6/2004 | Miller et al. | 351/163 |
| 2004/0114103 A1 | 6/2004 | Miller et al. | 351/165 |
| 2004/0145808 A1* | 7/2004 | Cathey et al. | 359/558 |
| 2004/0230299 A1 | 11/2004 | Simpson et al. | 623/6.11 |

FOREIGN PATENT DOCUMENTS

| | | |
|---|---|---|
| WO | WO 99/57599 | 11/1999 |
| WO | WO 01/35880 | 5/2001 |
| WO | WO 03/012528 | 2/2003 |
| WO | WO 03/032825 | 4/2003 |
| WO | WO 03/052492 | 6/2003 |
| WO | WO 03/076984 | 9/2003 |

OTHER PUBLICATIONS

Fitzgerrell, A.R. et al, "Defocus transfer function for circularly symmetric pupils"; *Applied Optics Opt. Soc. America, U.S.A.*, vol. 36, No. 23, 1997, pp. 5796-5804.

Varant, C. et al; "Imaging properties of defocused partitioned pupils"; *Journal of the Society of America, Optics and Image Science*, vol. 2, No. 6, 1985, pp. 799-802.

* cited by examiner

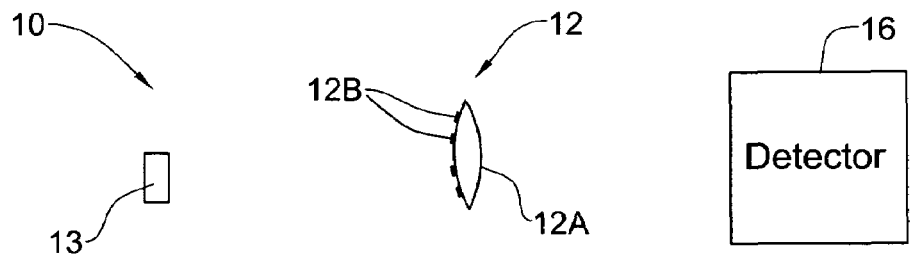
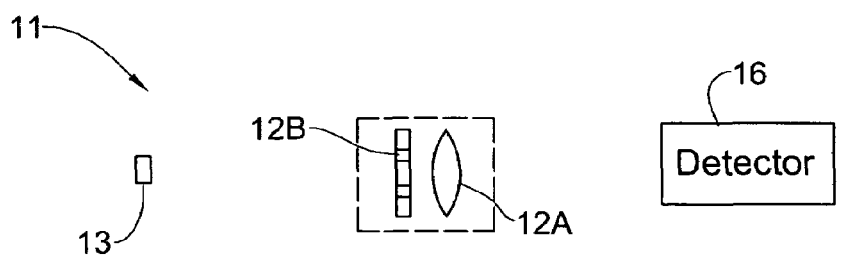
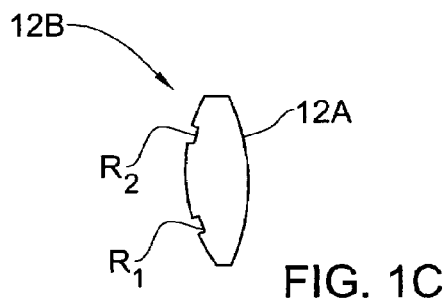
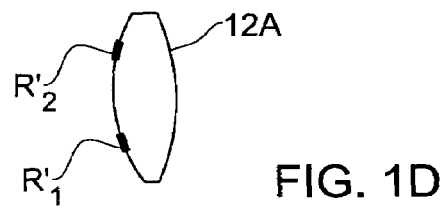
FIG. 1A
FIG. 1B
FIG. 1C
FIG. 1D
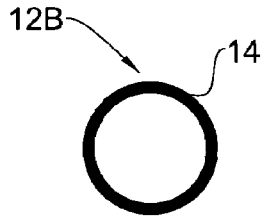
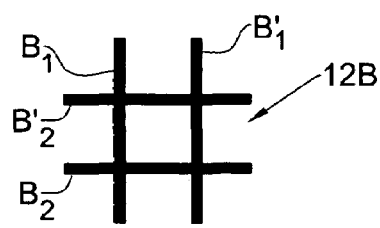
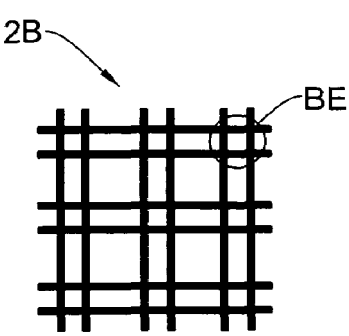
FIG. 2A
FIG. 2B
FIG. 2C

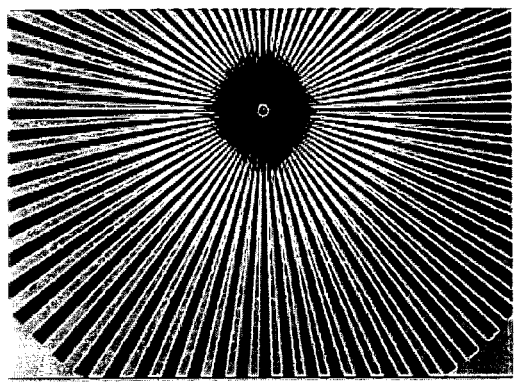 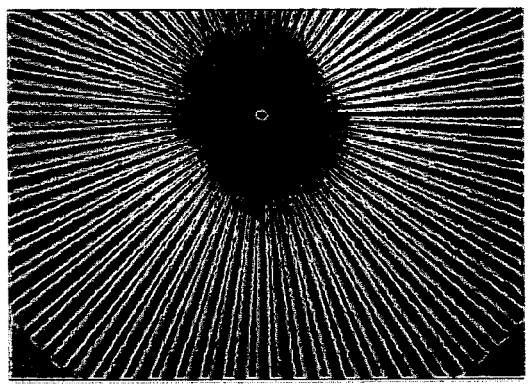
FIG.7A  FIG. 7B
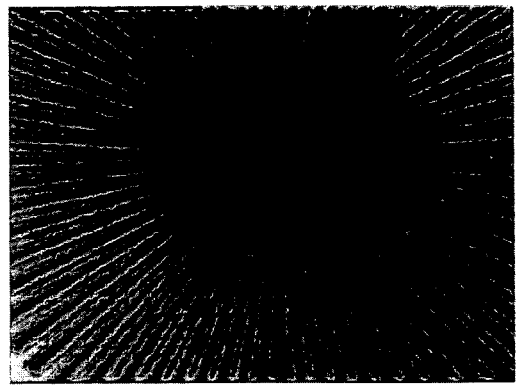 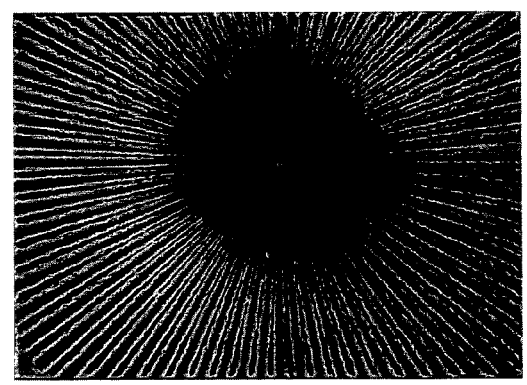
FIG.7C  FIG. 7D

OPTICAL METHOD AND SYSTEM FOR EXTENDED DEPTH OF FOCUS

FIELD OF THE INVENTION

This invention is generally in the field of imaging systems, and relates to an imaging lens arrangement with increased depth of focus.

BACKGROUND OF THE INVENTION

Extending the depth of focus of imaging systems is a very important core technology allowing its incorporation into various applications, including inter alia medically related applications where elements, such as cameras, are to be inserted into the body in order to observe and detect problematic tissues; as well as ophthalmic industry including glasses for spectacles, contact lenses, intraocular lenses or other lenses inserted surgically into the eye. The extended depth of focus solution is also needed for optical devices like microscopes or cameras for industrial, medical, surveillance or consumer applications, where focusing of light is required and where today focusing is being implemented by a multitude of lenses with the need of relative displacement between the focusing arrangement and an image and/or object plane, by mechanical movement, either manually or electronically driven.

Various approaches have been developed for obtaining extended depth of focus of an optical system. One of the known approaches, developed by the inventor of the present invention, is disclosed in WO 03/076984. This technique provides an all-optical extended depth of field imaging. An imaging system produces images of acceptable quality of objects which are located at a wide variety of distances from the imaging system. A preferred embodiment of the imaging system includes an object, an auxiliary lens, a composite phase mask and a sensor arranged along an optical axis. Light from the object is focused by the auxiliary lens in tandem with the composite phase mask, producing an image which is incident on the detector. This technique is based upon placing a spatially highly resolved phase element on top of the lens aperture such that continuous set of focal length is generated.

Another approach is disclosed for example in the following publications: U.S. Pat. No. 6,069,738; U.S. Pat. No. 6,097,856; WO 99/57599; WO 03/052492. According to this approach, a cubic phase mask is used in the aperture plane, and digital post processing is required to realize a focused image. More specifically:

U.S. Pat. No. 6,069,738 discloses an apparatus and methods for extending depth of field in image projection systems. An optical system for providing an in-focus, extended depth of field image on a projection surface includes an encoded mask or light encoder for preceding the light to include object information (or, equivalently, information about the desired image), and an extended depth of field (EDF) mask, for extending the depth of field of the projection system. In addition to including object information, the encoded mask encodes the light from the light source to account for the variations introduced by the EDF mask in extending the depth of field, so that no post processing is required.

U.S. Pat. No. 6,097,856 discloses an apparatus and method for reducing imaging errors in imaging systems having an extended depth of field. An improved optoelectronic imaging system is adapted for use with incoherently illuminated objects, and which produces final images having reduced imaging error content. The imaging system includes an optical assembly for forming an intermediate image of the object to be imaged, an image sensor for receiving the intermediate image and producing an intermediate image signal, and processing means for processing the intermediate image signal to produce a final image signal having a reduced imaging error content. A reduction in imaging error content is achieved, in part, by including in the optical assembly a phase mask for causing the OTF of the optical assembly to be relatively invariant over a range of working distances, and an amplitude mask having a transmittance that decreases continuously as a function of distance from the center thereof. The reduction in imaging error content is also achieved, in part, by including in the processing means an improved generalized recovery function that varies in accordance with at least the non-ideal calculated IOTF of the optical assembly under a condition of approximately optimum focus.

WO 99/57599 discloses an optical system for increasing the depth of field and decreasing the wavelength sensitivity of an incoherent optical system> The system incorporates a special purpose optical mask into the incoherent system. The optical mask has been designed to cause the optical transfer function to remain essentially constant within some range from the in-focus position. Signal processing of the resulting intermediate image undoes the optical transfer modifying effects of the mask, resulting in an in-focus image over an increased depth of field. Generally the mask is placed at or near an aperture stop or image of the aperture stop of the optical system. Preferably, the mask modifies only phase and not amplitude of light, though amplitude may be changed by associated filters or the like. The mask may be used to increase the useful range of passive ranging systems.

WO 03/052492 discloses a technique providing extended depth of focus (EDF) to human eyes by modifying contact lenses, intraocular implants, or the surface of the eye itself. This is accomplished by applying selected phase variations to the optical element in question (for example, by varying surface thickness). The phase variations EDF-code the wavefront and cause the optical transfer function to remain essentially constant within some range away from the in-focus position. This provides a coded image on the retina. The human brain decodes this coded image, resulting in an in-focus image over an increased depth of focus.

Yet another approaches, disclosed for example in U.S. Pat. No. 6,554,424 (as well as U.S. patent application publications 20040114103; 20040114102; and 20030142268) and U.S. Pat. No. 4,955,904, utilize apodization of the aperture plane. More specifically, U.S. Pat. No. 6,554,424 describes a system and method for increasing the depth of focus of the human eye. The system is comprised of a lens body, an optic in the lens body configured to produce light interference, and a pinhole-like optical aperture substantially in the center of the optic. The optic may be configured to produce light scattering or composed of a light reflective material. Alternatively, the optic may increase the depth of focus via a combination of light interference, light scattering, light reflection and/or light absorption. The optic may also be configured as a series of concentric circles, a weave, a pattern of particles, or a pattern of curvatures. One method involves screening a patient for an ophthalmic lens using a pinhole screening device in the lens to increase the patient's depth of focus. Another method comprises surgically implanting a mask in the patient's eye to increase the depth of focus.

U.S. Pat. No. 4,955,904 describes a masked intraocular lens for implantation into a human eye. The mask, which blocks only part of the lens body, together with the pupil of the eye, defines a small aperture in the eye when the pupil is constricted, thereby increasing the depth of focus, as a pinhole camera does. When the pupil of the eye is dilated, additional light is allowed to pass through the pupil around the mask and to reach the retina to allow a person to see in dimmer light conditions. In one embodiment, the mask defines a small circular aperture and a larger exterior annulus; the small circular aperture has an additional power intermediate between that needed for distance and close vision. Also provided is a method for treating a patient with cataracts comprising replacing the patient's lens with the lens of the invention Some other vision improvement techniques are disclosed in the following patent publications:

U.S. Pat. No. 5,748,371 discloses extended depth of field optical systems. The system for increasing the depth of field and decreasing the wavelength sensitivity and the effects of misfocus-producing aberrations of the lens of an incoherent optical system incorporates a special purpose optical mask into the incoherent system. The optical mask has been designed to cause the optical transfer function to remain essentially constant within some range from the in-focus position. Signal processing of the resulting intermediate image undoes the optical transfer modifying effects of the mask, resulting in an in-focus image over an increased depth of field. Generally the mask is placed at a principal plane or the image of a principal plane of the optical system. Preferably, the mask modifies only phase and not amplitude of light. The mask may be used to increase the useful range of passive ranging systems.

WO 01/35880 discloses multifocal aspheric lens, an optical surface in close proximity to a person's pupil for correcting presbyopia, a method for obtaining that optical surface, and a laser surgery system to carry out the method. The optical surface includes a first vision area, a second vision area surrounding the first area, and a third vision area surrounding the second vision area, the first vision area having a first substantially single power, the second vision area having a range of powers, the third vision area having a second substantially single power distinct from the first single power, at least one of the first, second and third vision areas having an aspheric surface, and the other areas having spherical surfaces. The method includes reshaping the cornea to obtain this optical surface. The cornea may be reshaped on the anterior or an underlying surface by ablation or collagen shrinkage, wherein the ablation is performed by applying an excimer laser, surgical laser, water cutting, fluid cutting, liquid cutting or gas cutting technique. The method also includes obtaining this optical surface by placing a contact lens having the desired optical characteristics on the cornea. The laser surgery system includes a laser beam generator and a laser beam controller to regulate the beam striking the cornea to remove a selected volume of corneal tissue from a region in an optical zone of the cornea with the ablative radiation, thereby forming a reprofiled region which has a first vision area, a second vision area surrounding the first area, and a third vision area surrounding the second vision area.

U.S. Pat. No. 5,965,330 discloses methods for fabricating annular mask lens having diffraction-reducing edges. According to this technique, the lens body has an annular mask that forms a "soft edge" by gradually decreasing the transmissivity radially from the center aperture to the annular mask area. The methods introduce varying levels of a coloring agent (e.g., dye) into certain portions of the lens.

WO 03/012528 describes an apparatus for generating a light beam with an extended depth of focus. The apparatus includes a binary phase mask that generates a diffraction pattern including bright main ring and two side-lobe rings, an annular aperture mask that passes only part of the diffraction pattern, and a lens that causes the light passing through the annular aperture to converge towards and cross the optical axis. Where the converging light crosses the optical axis, constructive interference takes place, generating a light beam that has an extended depth of focus.

U.S. Pat. Nos. 5,786,883; 5,245,367 and 5,757,458 describe an annular mask contact lens designed to operate with the normal functioning of the human pupil. An annular mask forms a small pinhole-like aperture on the contact lens enabling continual focus correction. The outer diameter of the annular mask allows the wearer to transmit more light energy through the pupil as brightness levels decrease. The contact lens may be structured with two separate and distinct optical corrections, both at the small aperture region and in the region beyond the annular mask. Functional imaging is thus achieved for both bright and dim lighting, and over a wide range of viewing distances.

U.S. Pat. No. 5,260,727 discloses wide depth of focus intraocular and contact lenses. According to this technique, the lens power can be a constant but the amplitude and phase of the wave across the pupillary aperture are variables. The lens can be constructed by shading regions thereof in accordance with a mathematical function, e.g., a Gaussian distribution or Bessel function over a predetermined geometry, such as e.g., concentric, parallel or radial. The lens may be of single power or multiple power, e.g., of the bi-focal type.

U.S. Pat. No. 5,905,561 discloses an annular mask lens for vision correction having diffraction reducing edges. The lens body has an annular mask that forms a "soft edge" by gradually decreasing the transmissivity radially from the center aperture to the annular mask area.

U.S. Pat. No. 5,980,040 describes a pinhole lens and contact lens. The contact lens comprises an optically transparent lens body having a concave surface adapted to the patient's eye curvature and a convex surface. The lens has three regions: (1) an annular region of a first optical power; (2) at the center of said annular region, which is also at the optical center of said lens, a substantially pinhole-like aperture; and (3) a second larger annular region exterior to the first annular region.

U.S. Pat. No. 5,662,706 discloses a variable transmissivity annular mask lens for the treatment of optical aberrations, such as night myopia, spherical aberration, aniridia, keratoconus, corneal scarring, penetrating keratoplasty, and post refractive surgery complication. The lens has an annular mask having an aperture larger than conventional pinhole contact lens. The aperture having a "soft" inside edge and which mask has a gradually increasing transmissivity radially toward the outer edge of the mask.

U.S. Pat. No. 5,225,858 describes a multifocal ophthalmic lens adapted for implantation in the eye or to be disposed on or in the cornea. The lens has an optical axis, a central zone and a plurality of annular zones circumscribing the central zone. Two of the annular zones have a first region with a far vision correction power and a second region with a near vision correction power. In an IOL embodiment, the vision correction power between far and near is progressive, and each of the second regions has a major segment in which the near vision correction power is substantially constant. The power in the central zone varies.

U.S. Pat. No. 6,554,859 discloses an intraocular lens for implantation in an eye of a patient. The lens includes a multifocal optic and a movement assembly. The optic has maximum add power which is less than the add power required for full near vision for a pseudophakic eye. The movement assembly is coupled to the optic and is adapted to cooperate with the eye of the patient to effect accommodating movement of the optic in the eye. Lens systems including two optics and two movement assemblies are also provided. The intraocular lenses and lens systems are particularly useful when implanted in the eyes of a patient after removal of the natural lenses.

U.S. Pat. Nos. 6,576,012 and 6,537,317 disclose a binocular lens system for improving the vision of a patient. The system includes first and second ophthalmic lenses. Each of these lenses is adapted for implantation in an eye or to be disposed on or in the cornea. The first lens has a first baseline diopter power for distance vision correction and the second ophthalmic lens has a second baseline diopter power for other than distance vision correction. The ophthalmic lenses may be intraocular lenses which are implanted in the eyes of a patient or has natural lenses or following removal of the natural lenses.

U.S. Pat. No. 6,474,814 discloses a multifocal ophthalmic lens with induced aperture. The multifocal lenses are defined by nonconical aspheric optical surfaces. Various alternative surface shapes provide a central distance vision region surrounded by an optical step. The optical step has rapidly increasing power in the radial direction which creates an induced aperture through which the cortical elements of the vision system are induced to concentrate. The induced aperture results in increased clarity in distance vision. Nonconical aspheric optical surfaces are defined to produce the desired optical power distributions. These surface functions are also provided in form of polynomial series for simplicity of use in computer driven lathes for shaping contact lenses. This technique refers to contact lenses, scleral lenses, intraocular lenses, and lenses impressed or surgically shaped within the corneal tissue.

U.S. Pat. No. 6,527,389 describes an improved multifocal ophthalmic lens, which has a plurality of alternating power zones with a continuously varying power within each zone, as well as in transition from one zone to another. In other words, a plurality of concentric zones (at least two) are provided in which the variation from far to near vision correction is continuous, i.e., from near correction focal power to far correction focal power, then back to near, and again back to far, or vice versa. This change is continuous (progressive), without any abrupt correction changes, or "edges". Two versions of this technique are disclosed. In the first version continuous, alternating power variation is accomplished by a continuously changing curvature of the lens posterior surface, thereby altering the angle of impact of light rays on the eye. In the second version continuous, alternating power variation is accomplished by creating non-homogeneous surface characteristics having refractive material indexes which continuously vary in the lens radial direction (out from the optical axis).

U.S. Pat. No. 5,715,031 discloses concentric aspheric multifocal lens designs which use a combination of an aspheric front surface, which results in aberration reduction and contrast vision enhancement, along with a concentric multifocal back surface, to produce a lens design which affords clear vision at a distance and also near without a loss in contrast which is generally typical of prior art simultaneous vision, concentric multifocal lens designs. The aspheric surface improves the modulation transfer function (MTF) of the lens eye combination which improves the focus and contrast of both distance and near images. The design form is valid for contact lenses and intraocular lenses.

U.S. Pat. No. 6,024,447 discloses an enhanced monofocal ophthalmic lens for providing a monofocal vision correction power with an enhanced depth of focus. The lens is adapted to be implanted into an eye, placed over the eye, or to be disposed in a cornea of the eye. The ophthalmic lens includes a baseline diopter power for far vision correction, a first zone having a first vision correction power, and a second zone having a second vision correction power. The second zone is located radially outwardly of the first zone. The first zone includes a near vision correction power, and the second zone includes a far vision correction power. A maximum diopter value of the first zone is approximately 0.7 diopters above the baseline diopter, and a minimum diopter value of the second zone is approximately 0.5 diopters below the baseline diopter power. The first zone is adapted for focusing light at a first predetermined distance from the retina of the user, and the second zone is adapted for focusing light at a second predetermined distance from the retina of the user. The second predetermined distance is approximately opposite and equal to the first predetermined distance. A third zone, which is substantially similar to the first zone, is located radially outwardly of the second zone, and a fourth zone, which is substantially similar to the second zone, is located radially outwardly of the third zone. A third vision correction power of the third zone is approximately the same as the first vision correction power of the first zone, and a fourth vision correction power of the fourth zone is approximately the same as the second vision correction power of the second zone.

U.S. Pat. No. 6,451,056 describes an intraocular lens for increased depth of focus. The intraocular lens provides substantially increased depth of focus for accurate near and far vision with an optic much thinner than a natural lens, the lens being rigid, vaulted posteriorly and adapted for posterior positioning in the capsular bag. The optic is positioned substantially farther from the cornea than a natural lens, so that a cone of light exiting the optic to impinge upon the retina is much smaller than a cone of light from a natural lens. Typically, the optic may be about 1.0 mm thick and its distance from the cornea 7.0–8.0 mm.

WO 03/032825 discloses a method of designing a contact lens or other correction for providing presbyopia correction to a patient. The method relies on wavefront aberration measurement data for providing a best form correction. Preferably the correction is in the form of a multifocal translating style alternating vision contact lens or a simultaneous vision style correcting lens. A method for designing a correction for improving a person's vision is directed to correcting higher order aberrations in such a manner that a residual amount of the higher-order rotationally symmetric aberration is greater than a residual amount of the higher-order rotationally asymmetric aberration after the correction. The design method is directed to correcting asymmetric higher order aberrations induced by decentering of a multifocal contact lens that has residual spherical aberration which provides increased depth of field.

EP 0369561 discloses a system and process for making diffractive contact and intra-ocular lenses. The optical system includes the following principal elements in optical alignment along an optical axis, for accomplishing the indicated steps of the process: a laser for emission of ultraviolet light along the optical axis; a zone plate mask in the path of irradiation by the laser; and an imaging lens to project, with radiation from the laser, an image of the mask on the concave inner surface of an eye lens mounted coincident with the image surface of the optical system, thereby ablating the eye lens imagewise of the mask to generate a phase zone plate on the eye lens. The laser beam scans the zone plate mask to generate a composite image on the image surface. Alternatively, the phase zone plate is generated on the concave surface of a glass blank at the image surface to form a tool from which molds, and in turn lenses, are replicated. The light source is an argon fluoride excimer laser, emitting at 193 nm. The lens is a variable magnification lens to project various size images of the mask for producing zone plates of various powers as desired.

The known techniques, however, suffer from such drawbacks as unavoidable scattering of a significant part of energy towards the outer regions of a field of view of the system; the need for digital post processing; damaging the spatial frequencies transmission and the energetic efficiency.

SUMMARY OF THE INVENTION

There is accordingly a need in the art for an all-optical extended depth of focus technique.

The present invention solves the above problems by providing an imaging arrangement utilizing an optical element located adjacent to, attached to the surface of, or incorporated within an effective aperture of the imaging arrangement. It should be noted that the term "effective aperture of the imaging arrangement" used herein signifies a light collecting aperture, which may be the actual size of an imaging lens itself or an aperture in front of the imaging lens, as the case may be, for example the eye's pupil in ophthalmic applications.

The optical element of the present invention is configured as a phase-affecting, non-diffractive, thin-layer optical element that codes the lens aperture so as to provide an all-optical effect of extending the depth of focus. The optical element may be configured as a phase-only element or as a phase and amplitude affecting element. The term "all-optical" used herein signifies that a need for image processing is eliminated or at least substantially reduced.

The optical element is thus insensitive to wavelength and polychromatic illumination, does not scatter energy towards the outer regions of the field of view thus providing a very high energetic efficiency at the region of interest (close to 100%), and does not require apodization. It is important to note that such a high efficiency cannot be achieved by a diffractive optical element even if it is phase-only element, because of the divergence of light to unwanted diffraction orders. Since the technique of the present invention does not require digital post processing, it is adequate for ophthalmic applications or other "non-computer" based applications.

The optical element of the present invention is configured to define a mask (preferably a binary mask) of spatially low frequencies transitions. This may actually be achieved by designing the optical element so as to define at least one transition region (e.g., line or circle), to be surrounded by regions of the imaging lens, in the plane of the imaging lens. This at least one region of the optical element together with the imaging lens' regions define a predetermined pattern formed by spaced-apart optically transparent features of different optical properties (i.e., differently affecting the phase of light passing through the imaging lens arrangement).

The position(s) of the transition region(s) of the optical element within the imaging lens plane (i.e., the affective aperture plane) are selected, considering at least the affective aperture size of the imaging lens. These positions are appropriately selected so as to generate proper phase interference relation between light portions passing through different regions of the lens arrangement corresponding to the different features of the pattern, to thereby enable reducing a quadratic phase factor resulting from light getting out of focus of the imaging lens and thus maximize a defocused optical transfer function (OTF) of the imaging lens arrangement.

As indicated above, in order to design the optimal configuration for the extended depth of focus (EDOF) optical element, the effective aperture of the imaging lens is to be taken into consideration. The optical power distribution of the imaging lens and/or focal length may also be taken into consideration: since the EDOF has no optical power, it may be added to an imaging lens in order to shift the range of extended depth of focus around a certain given optical power.

The optimal geometry and dimensions of the EDOF element (i.e., at least one transition region) are determined using an optimization algorithm (based on a numerical or analytical approach, resulting in a spatially low frequency all-optical extended depth of focus), which determines N position(s) for the transition region(s) of the element within a given imaging lens (i.e., for a given effective aperture size).

Considering ophthalmic applications, where the effective aperture of the lens (eye pupil, or contact lens, or lens of spectacles) can be defined by a certain relatively narrow range of values common for most of patients, the EDOF of the present invention can be designed to be universal for a great amount of patients. Such a universal EDOF is configured to allow the depth of focus region equivalent to 5 diopters for the effective aperture of 2–3 mm. For a smaller percentage of patients having a higher difference between the near and far vision, the design of the EDOF element takes into account the optical power of the imaging lens with which the element is associated.

The position of the transition(s) (being pi-phase transition for a certain wavelength for which the EDOF is designed) generates invariance to quadratic phase distortions (which multiply the CTF of the imaging lens, corresponding to the effect of getting out of focus) under the operation of auto correlation. Due to the fact that the aperture mask (formed by the EDOF and imaging lens) is constructed out of spatially low-frequency transitions, it does not spread energies away from the zero order of diffraction and its energetic efficiency is close to 100%.

It should be noted that auto correlating the CTF is done to compute the optical transfer function (OTF) of the imaging system. The position of the EDOF transition(s) may be computed using iterative algorithm in which M positions are examined and eventually those of them are selected, which provide maximal contrast of the OTF under a set of out of focus locations. The meaning of OTF's contrast optimization (maximizing) is actually having the out of focused OTF bounded as much as possible away from zero.

The extended depth of focus (EDOF) element of the present invention is configured to generate proper phase interference relation allowing significant cancellation of the quadratic phase factor obtained due to getting out of focus. The EDOF element is a phase-affecting element (e.g., phase-only binary mask element), which is neither a refractive nor a diffractive element. In contrast to a refractive element, the EDOF filter of the present invention can be produced as a thin phase layer constructed in a low-cost lithographic technique with the thickness of the phase layer being of only one wavelength (e.g., around 0.5 micron in the case of ambient light illumination), similar to the fabrication approaches used for the conventional diffractive optical elements. On the other hand, in contrast to diffractive optical elements, the EDOF of the present invention has the spatial feature(s) of very low frequency. The element contains only very limited number of features and periods at low spatial frequency (period of about 1,000 wavelengths). The property of the optical element of the present invention allows for obtaining truly energetic efficient EDOF, since not only all the energy is passed through the element itself (it is substantially phase only) but also all of the energy is concentrated at the proper transversal and longitudinal region of interest (in contrast to a diffractive element that has energetic split either between multiple longitudinal focal planes or between traversal diffraction orders).

Hence, high energetic efficiency (close to 100%) of the optical element of the present invention provides extended depth of focus, in contrast to approaches based on the use of diffractive optical elements that split the energy between several diffraction orders/focal planes and that are basically equivalent to smaller lens aperture (also having larger depth of focus). In addition, the low spatial frequency of the invented approach eliminates its sensitivity to wavelength and polychromatic illumination which is a problematic topic with diffractive optical elements. Additionally, it is important to note that the invented approach is an all-optical technique that does not require numerical computation, and when it is used for ophthalmic applications it does not assume brain based decoding or adaptation process since an extended depth of focus image is identical to the image of an object itself.

There is thus provided according to one broad aspect of the present invention, an imaging arrangement comprising: an imaging lens having a certain affective aperture, and an optical element associated with said imaging lens and configured to provide an extended depth of focus of the imaging arrangement, said optical element being configured as a phase-affecting, non-diffractive optical element defining a spatially low frequency phase transition, said optical element together with the imaging lens defining a predetermined pattern formed by spaced-apart optically transparent features of different optical properties, position of at least one phase transition region of the optical element within the imaging lens plane being determined by at least a dimension of said affective aperture.

According to another broad aspect of the invention, there is provided an imaging arrangement comprising: an imaging lens having a certain affective aperture, and an optical element associated with said imaging lens and configured to provide an extended depth of focus of the imaging arrangement, said optical element being configured as a phase-only, non-diffractive binary mask defining a spatially low frequency phase transition, said optical element together with the imaging lens defining a predetermined pattern formed by spaced-apart optically transparent features of different optical properties, position of at least one phase transition region of the optical element within the imaging lens plane being determined by at least a dimension of said affective aperture.

According to yet another aspect of the invention, there is provided an imaging arrangement comprising: an imaging lens having a certain affective aperture, and an optical element associated with said imaging lens and configured to provide an extended depth of focus of the imaging arrangement, said optical element being configured as a phase-affecting, non-diffractive optical element defining a spatially low frequency phase transition, said optical element together with the imaging lens defining a predetermined pattern formed by spaced-apart optically transparent features of different optical properties, position of at least one phase transition region of the optical element within the imaging lens plane being determined by at least a dimension of said affective aperture such that the optical element produces proper phase interference relation between light portions passing through different regions of the imaging arrangement corresponding to the different features of the pattern to thereby reduce a quadratic phase factor resulting from light getting out of focus of the imaging lens and maximize a defocused optical transfer function (OTF) of the imaging lens arrangement by providing the out of focus OTF as much as possible away from zero.

According to yet another broad aspect of the invention, there is provided an imaging arrangement comprising an imaging lens having a certain affective aperture, and an optical element associated with said imaging lens and configured to provide an extended depth of focus of the imaging arrangement, said optical element being configured as a phase-affecting, non-diffractive element defining a certain pattern of spatially low frequency phase transitions within a plane of the imaging lens, such that said optical element together with the imaging lens determine a predetermined pattern formed by spaced-apart optically transparent features differently affecting phase of light passing through the imaging arrangement, positions of the phase transitions of the optical element within the imaging lens plane being determined by at least a dimension of said affective aperture to reduce sensitivity of the imaging arrangement to shifts of a Coherent Transfer Function (CTF) of the imaging lens while getting out of focus.

According to yet another aspect of the invention, there is provided an imaging arrangement for creating an image of an object on a detector plane, the system comprising an imaging lens arrangement formed by an imaging lens having a certain affective aperture and an optical element configured to provide an extended depth of focus of the imaging arrangement, said optical element being configured as a phase-affecting, non-diffractive element defining a spatially low frequency phase transition, said optical element together with the imaging lens defining a predetermined pattern formed by spaced-apart optically transparent features of different optical properties, position of at least one phase transition region of the optical element within the imaging lens plane being determined by at least a dimension of said affective aperture such that the optical element produces proper phase interference relation between light portions passing through different regions of the imaging arrangement corresponding to the different features of the pattern to thereby enable reducing a quadratic phase factor resulting from light getting out of focus of the imaging lens and maximize a defocused optical transfer function (OTF) of the imaging arrangement.

According to yet another aspect of the invention, there is provided an optical element for use with an imaging lens for extending depth of focus of imaging, the optical element being configured as a phase-affecting, non-diffractive optical element defining a predetermined pattern of spatially low frequency phase transitions, said pattern being defined by an affective aperture of the given imaging lens.

According to yet another aspect of the invention, there is provided an optical element for use with an imaging lens for extending depth of focus of imaging, the optical element being configured as a phase-only, non-diffractive binary element defining a predetermined pattern of spatially low frequency phase transitions, said pattern being defined by an affective aperture of the given imaging lens. According to yet another aspect of the invention, there is provided an optical element for extending depth of focus of imaging, the optical element being configured as a phase-affecting, non-diffractive optical element defining a spatially low frequency phase transition.

According to yet another aspect of the invention, there is provided an optical element for extending depth of focus of imaging, the optical element being configured as a phase-affecting, non-diffractive optical element defining a spatially low frequency phase transition, the optical element defining a predetermined pattern of phase transition regions, said transition regions being arranged in accordance with an affective aperture of a given imaging lens for which the optical element is designed, so as to provide said transition regions of the optical element within predetermined positions in the imaging lens plane, to provide periodic replication of a lateral phase shape of a light field propagating through the imaging lens with said optical element.

According to yet another aspect of the invention, there is provided an optical element for extending depth of focus of imaging, the optical element being configured as a phase-only, non-diffractive binary element defining a spatially low frequency phase transition, the optical element defining a predetermined pattern of phase transition regions, said transition regions being arranged in accordance with an affective aperture of a given imaging lens for which the optical element is designed, so as to provide said transition regions of the optical element within predetermined positions in the imaging lens plane, to provide periodic replication of a lateral phase shape of a light field propagating through the imaging lens with said optical element.

According to yet another aspect of the invention, there is provided a method for providing a certain extended depth of focus of an imaging system, the method comprising applying an aperture coding to an imaging lens having a certain effective aperture, by applying to the imaging lens a phase-affecting non-diffractive optical element configured to define a spatially low frequency phase transition arrangement and thereby provide a predetermined pattern of spaced-apart substantially optically transparent features of different optical properties within the imaging lens plane, thereby producing phase interference relation between light portions passing through different regions of the lens arrangement corresponding to the different features of the pattern so as to reduce a quadratic phase factor resulting from light getting out of focus of the imaging lens and maximize a defocused optical transfer function (OTF) of the imaging lens arrangement.

According to yet another aspect of the invention, there is provided a method for providing a certain extended depth of focus of an imaging system, the method comprising designing a phase-affecting non-diffractive optical element to be used with an imaging lens having a certain effective aperture, said designing comprising selecting N positions for phase transitions within the imaging lens effective aperture as those providing maximal contrast of an Optical Transfer Function (OTF) of the imaging system under a set of out of focus locations, thereby providing the out of focus OTF as much as possible away from zero.

BRIEF DESCRIPTION OF THE DRAWINGS

In order to understand the invention and to see how it may be carried out in practice, preferred embodiments will now be described, by way of non-limiting example only, with reference to the accompanying drawings, in which:

FIG. 1A is a schematic illustration of an example of an imaging system utilizing an imaging lens arrangement configured according to the present invention;

FIG. 1B schematically illustrates another example of an imaging lens arrangement of the present invention;

FIGS. 1C and 1D exemplifies the optical element of the present invention as implemented integral with an imaging lens;

FIGS. 2A to 2C show three examples, respectively, of the contour of the optical element of the present invention suitable to be used in the imaging lens arrangement;

FIGS. 7A to 7D show experimental results for imaging a Rosette with and without the EDOF element of the invention: FIG. 7A corresponding to the in focus position of Rosette with no EDOF element, FIG. 7B corresponds to in-focus position with the EDOF element, FIG. 7C corresponds to the out of focus position of Rosette with no EDOF element, and FIG. 7D corresponds to the out of focus position with the EDOF element;

DETAILED DESCRIPTION OF THE INVENTION

Figure 3A:
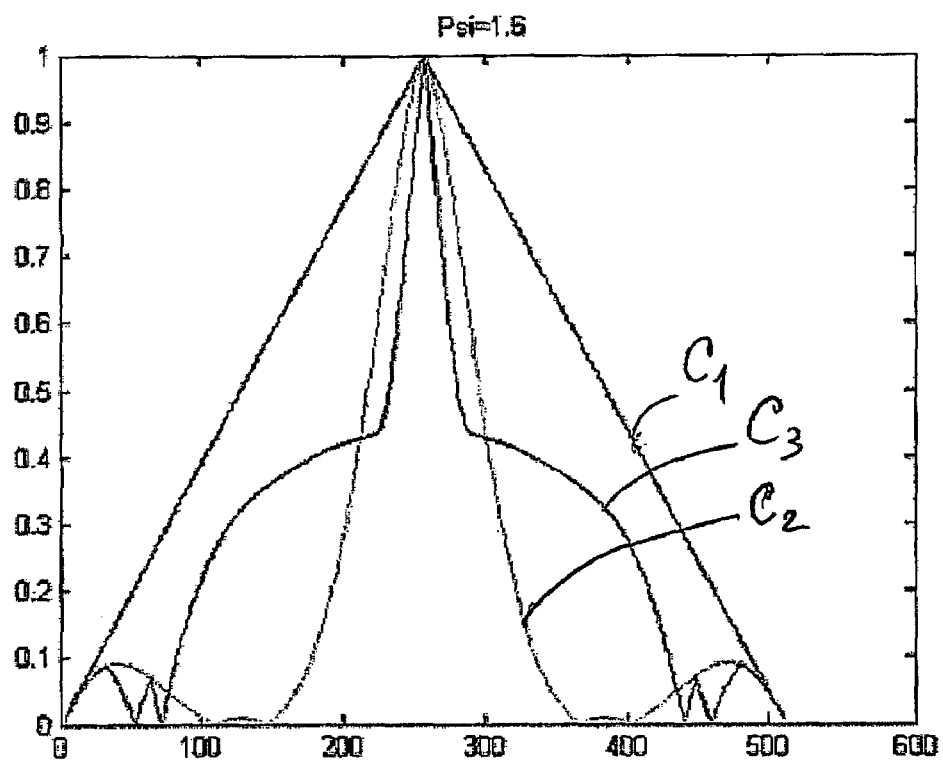
FIGS. 3A to 3D illustrate the effect of the present invention as compared to the conventional approach.
Figure 3B:
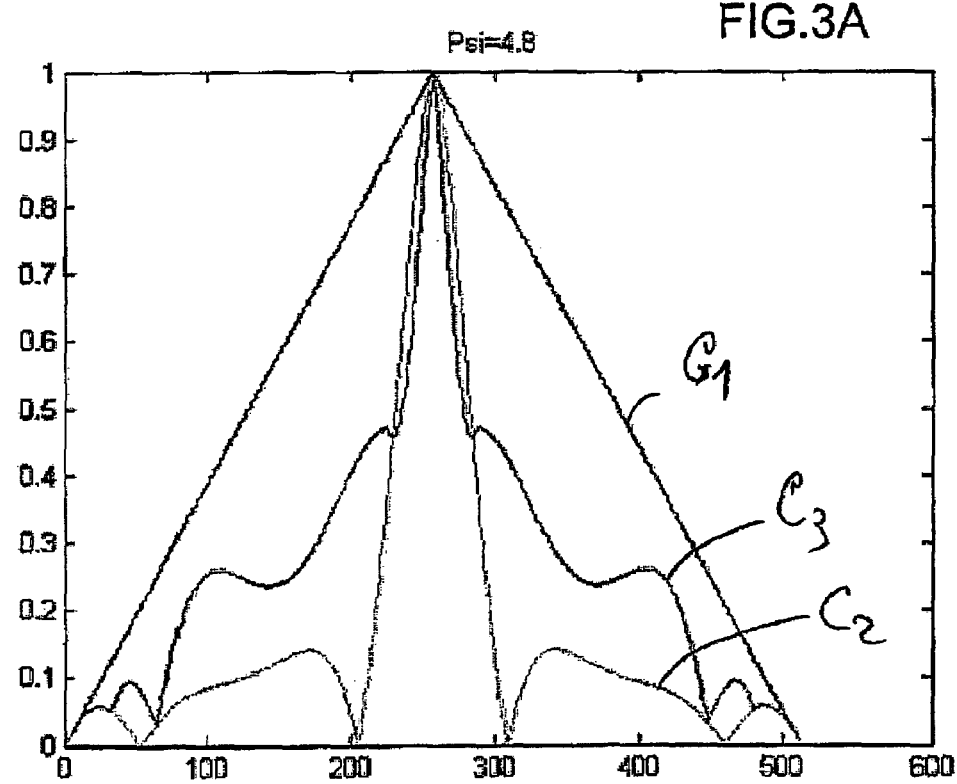
Figure 3C:
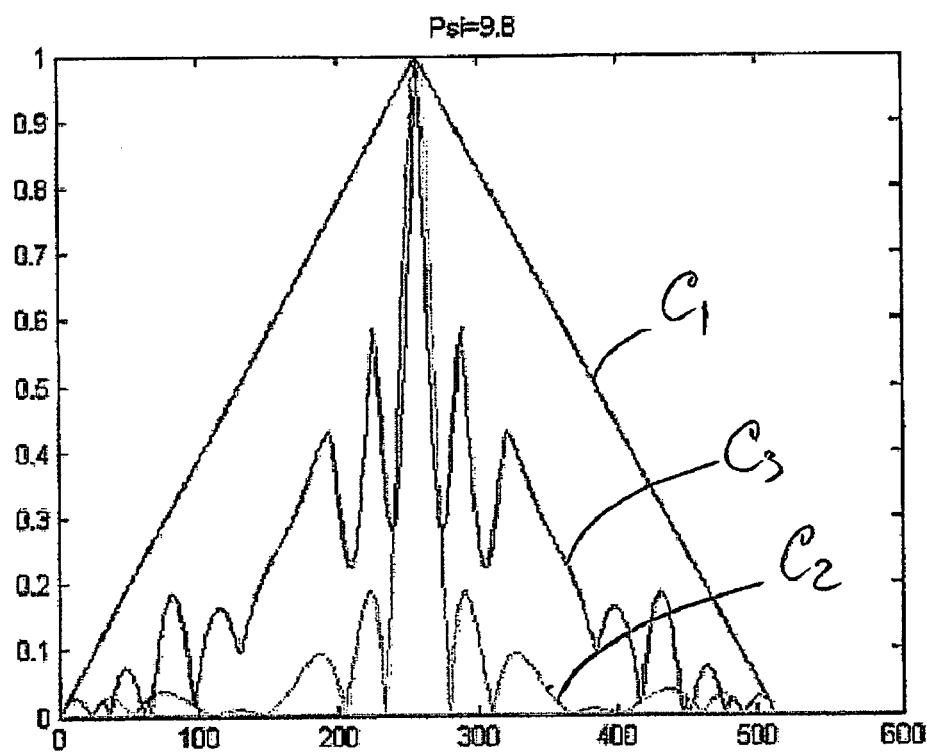
Figure 3D:
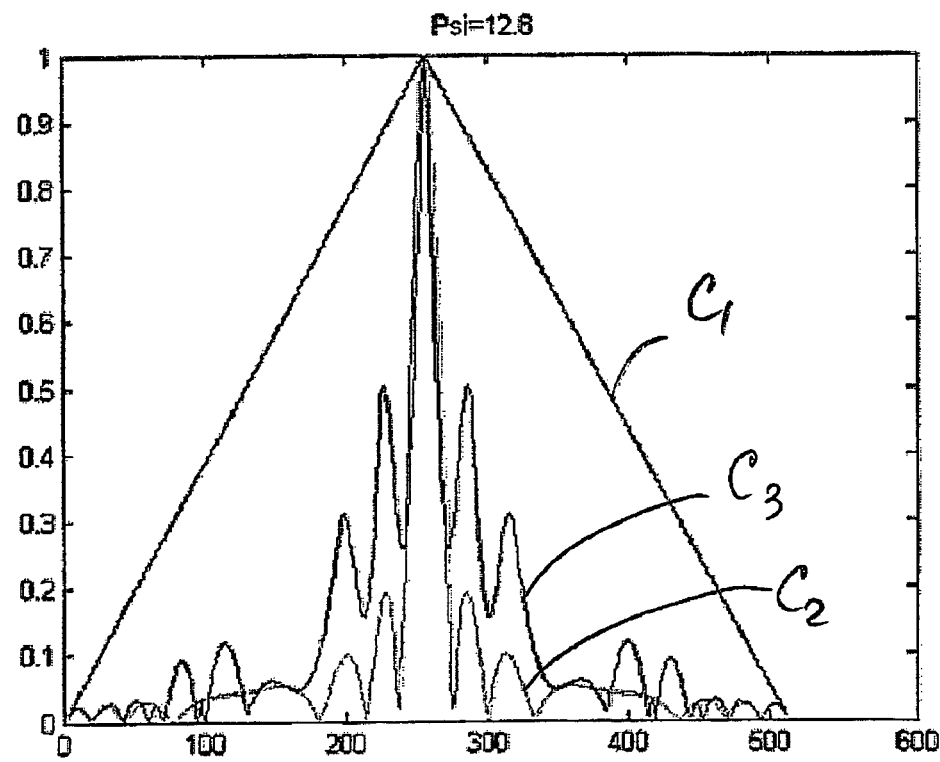
Figure 4A:
FIGS. 4A to 4I exemplify face images obtained with the out of focus parameter $4\psi/D^2$ varying from $-0.2$ (FIG. 4A) up to 0.2 (FIG. 4I) at steps of 0.05, for the case where the optical element of the present invention is used.
Figure 4B:
Figure 4C:
Figure 4D:
Figure 4E:
Figure 4F:
Figure 4G:
Figure 4H:
Figure 4I:
Figure 5A:
FIGS. 5A to 5I exemplify face images obtained with the out of focus parameter $4\psi/D^2$ varying from $-0.2$ (FIG. 5A) up to 0.2 (FIG. 5I) at steps of 0.05, for the case where no optical element of the present invention is used.
Figure 5B:
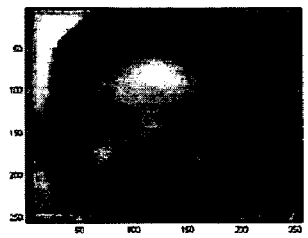
Figure 5C:
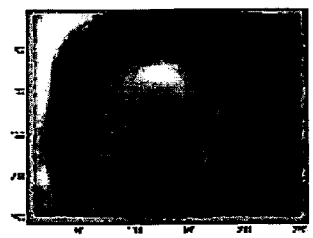
Figure 5D:
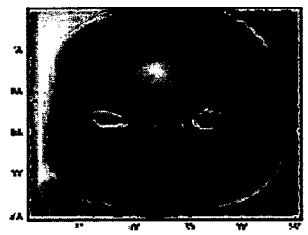
Figure 5E:
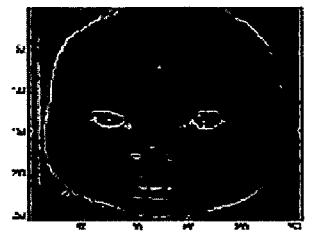
Figure 5F:
Figure 5G:
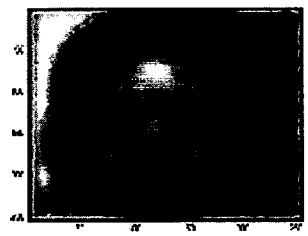
Figure 5H:
Figure 5I:
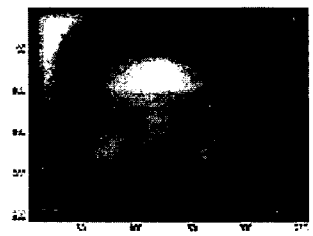

Referring to FIG. 1A, there is schematically illustrated an imaging system 10 utilizing an imaging lens arrangement 12 of the present invention. The imaging system 10 is formed by an object 13 that is to be imaged, the imaging lens arrangement 12, and a light detector unit 16. The lens arrangement 12 includes an imaging lens 12A having a certain effective aperture D (which in the present example if the lens diameter), and an optical element 12B.

The optical element 12B is configured in accordance with the parameters of the lens 12A, i.e., its effective aperture and optionally also the optical power distribution and/or focal length. The optical element 12B is configured as a phase-affecting non-diffractive mask. Preferably, as shown in the present example, the mask 12B is implemented integral with the lens, namely as a pattern on the lens surface.

Generally, the mask 12B may be a separate element attached to the imaging lens or located close thereto. This is illustrated in FIG. 1B showing an imaging system 100 utilizing a lens arrangement 112 includes an imaging lens 12A and a phase-affecting non-diffractive optical element 12B located close to the lens in front thereof. Preferably, the element 12B is configured as a phase-only binary mask. It should, however be noted that generally the element 12B may be configured as a phase and amplitude mask.

The optical element 12B is configured to define at least one spatially low frequency transition region, and the element 12B together with the lens 12A regions define a predetermined pattern of spaced-apart substantially optically transparent features differently affecting the phase of light passing therethrough. The pattern is thus formed by one or more transition regions of the optical element, spaced by the regions of the lens, in the imaging lens plane. The transition regions are pi-phase transitions for a certain wavelength for which the mask 12B is designed. The arrangement of these transition regions (positions within the lens 12A plane) is determined by the effective aperture of the given imaging lens 12A (and possibly also optical power of the lens) so as to maximize the defocused OTF of the entire imaging arrangement. To this end, the pattern is such as to generate proper phase interference relation between light portions passing through different regions of the lens arrangement to thereby enable reducing a quadratic phase factor resulting from light getting out of focus of the imaging lens.

As shown in FIGS. 1C and 1D, the optical element may be implemented as a surface relief on the imaging lens (FIG. 1C), namely, a pattern of spaced-apart regions $R_1$ and $R_2$ of variable lens thickness; or as a pattern of lens regions $R'_1$ and $R'_2$ made of materials with different refractive indices $n_1$ and $n_2$ (FIG. 1D). In the case of different refractive index materials, a certain optically transparent material of a refractive index different from that of the lens may be coated on selective spaced-apart regions of the lens surface.

FIGS. 2A to 2C show two specific but not limiting examples, respectively, of the contour of the optical element 12B. In the example of FIG. 2A, the mask 12B is designed as an annular transition region 14 (generally, at least one such region; an array of concentric rings may be used as well). In the example of FIG. 2B the mask is designed as a grid formed by two mutually perpendicular pairs of bars (lines) $B_1$–$B'_1$ and $B_2$–$B'_2$. In the example of FIG. 2C, the element 12B is a mask formed by a two-dimensional array of basic grid-elements BE. For example, the transition regions along the bar line are pi-phase transitions and the regions of intersection between the perpendicular bars are zero-phase transitions. The optimized contour for the optical element is obtained solving an algorithm, which will be described further below.

It should be noted that the mask (pattern) may and may not be symmetrical relative to the center of the lens. In such an arrangement, for example, the four π-phase bars, two vertical (along Y-axis) and two horizontal (along X-axis) bars, that are illustrated in FIG. 2A, may be shifted transversally along the x-y plane to be not centered around the center of the lens.

It should also be noted, although not specifically shown, that the pattern may be configured to define microstructures inside the phase transition region (e.g., inside the pi-phase transition ring of FIG. 2A), namely, each phase transition region may be of a variable spatially low frequency of phase transition such as for example π/2, π, . . . .

The present invention provides the EDOF element 12B in the form of a mask of N segments within the effective aperture of the imaging lens 12A. It should be understood that instead of having a mask that blocks energy in some of segments and transmits in the other, the invention provides the substantially phase-only, non-diffractive mask 12B, that is either 1 or (−1) depending on the segment.

As indicated above, the mask 12B is designed to maximize the defocused OTF of the imaging system, by generating invariance to quadratic phase factor (which factor is generated when the image is defocused and multiplies the CTF of the imaging lens). To this end, in order to optimally design the mask 12B, a search is made for the segments that will obtain the transmission value of (−1) such that the OTF, due to the out of focus distortion, is bounded as much as possible away from zero. Since the mask 12B is a binary phase mask, no energy efficiency consideration is used (the transmission is 100%). Following these criteria, a search is made over all the possibilities and combinations for the aperture coding mask. The out of focus distortion is modeled by multiplying the aperture with the following expression:

$$\tilde{D}(v) = \exp\left(\frac{i4\Psi v^2}{D^2}\right) \quad (1)$$

wherein $\tilde{D}(v)$ is the CTF of the imaging lens 12A corresponding to the out of focus position of the object being imaged, D is the diameter of the imaging lens 12A (generally, the effective aperture of the lens), v is the coordinate of the aperture of the lens (in the plane of CTF), and ψ is the phase factor representing the amount of getting out of focus:

$$\Psi = \frac{\pi D^2}{4\lambda}\left(\frac{1}{u} + \frac{1}{v} - \frac{1}{F}\right) \quad (2)$$

wherein λ is the wavelength, u is the distance between the imaging lens 12A and the object 13, v is the distance between the imaging lens 12A and the sensor 16 (detector), and F is the focal length of the imaging lens. It should be noted that the term "imaging lens" refers here to the effective aperture thereof.

When imaging condition is fulfilled:

$$\frac{1}{u} + \frac{1}{v} = \frac{1}{F} \quad (3)$$

the distortion phase factor ψ equals zero.

The OTF is computed by auto-correlating the CTF with itself:

$$\text{OTF}(v) = \text{CTF}(v) \otimes \text{CTF}(v) \quad (4)$$

The auto correlation operation consists of shifting two CTF functions to the opposite directions, respectively, and then multiplying and summing the result. The so-obtained OTF relates to a spatial frequency that corresponds to the amount of the shift. At high frequencies (large shifts), the multiplication and the summing are averaged to zero in the case of out of focus. Hence, the OTF does not transmit high frequencies when the image is defocused.

The phase mask (e.g., ring) of the present invention is aimed at reducing the high-frequency cancellation at large shifts of the CTF (the OTF is an auto correlation of the CTF). To this end, the mask is configured to invert the sign of part of the light field that before (i.e., pure lens with no EDOF correction) was averaged to zero (and this is why the OTF did not transmit the high spatial frequencies).

The OTF is the Fourier transform of the intensity point spread function, and it is used to express the spatial-frequencies transmission function for intensity, when incoherent illumination is applied. Thus, the mathematical formulation for maximizing the OTF is as follows:

$$\max_{a_n}\left\{\min\left\{\left[\tilde{D}(v)\sum_{n=1}^{N}a_n\mathrm{rect}\left(\frac{v-n\Delta v}{\Delta v}\right)\right]\otimes\left[\tilde{D}(v)\sum_{n=1}^{N}a_n\mathrm{rect}\left(\frac{v-n\Delta v}{\Delta v}\right)\right]\right\}\right\} \quad (5)$$

i.e., find the values for $a_n$ that provide maximum for the minima of the auto correlation expression where $a_n=(1,-1)$ (it equals either 1 or −1).

It should be noted that the above-described iterative numerical algorithm is a specific but not limiting example of defining the EDOF element configuration. Other techniques can be used as well, for example numerical approached based on entropy minimization, or maximal likelihood, or other numerical or analytical approaches, resulting in a spatially low frequency all-optical extended depth of focus.

FIGS. 3A to 3D illustrate the effect of the present invention. Three examples of absolute value of the OTF (called Modulation Transfer Function—MTF) are obtained for different phase factor values: $\psi=1.6$ in FIG. 3A; $\psi=4.8$ in FIG. 3B; $\psi=9.8$ in FIG. 3C and $\psi=12.8$ in FIG. 3D. In each of these figures, curve $C_1$ corresponds to the MTF while at the in-focus state, curve $C_2$ corresponds to the defocused MTF of an imaging system without the use of the correction optical element (EDOF element) of the present invention (mask 12B in FIG. 1), and curve $C_3$ corresponds to the defocused MTF of the system with the correction element.

The transversal invariance may be obtained using the phase element producing periodic replication of the phase shape, namely lateral replication of the phase shape. Turning back to FIG. 2C exemplifying a mask formed by a two-dimensional array of basic elements BE, when large lateral shifts (high frequencies) exclude part of the phase shape, a complimentary part is inserted from another spatial period of the mask thus producing the phase period by replication. The replication of the basic period of the transitions (that of the basic element BE) thus reduces the sensitivity to lateral shifts. The longitudinal invariance is obtained as follows: Given the longitudinal distance between the phase element and a sensor (the imaging lens plane or the effective aperture plane), which is the lens of the human eye in case of ophthalmic applications, free space propagation of the mask function for this distance is considered. The result is a phase and amplitude distribution. The amplitude is dropped, leaving only the phase profile. In many cases, binarization of the phase function may provide sufficiently good results as well. The binarization realizes spatial mask which is easier for fabrication.

Reference is made to FIGS. 4A–4I and FIGS. 5A–5I illustrating how a face image looks like when the defocusing parameter $4\psi/D^2$ is varied from −0.2 (FIGS. 4A and 5A) up to 0.2 (FIGS. 4I and 5I) at steps of 0.05. FIGS. 4A–4I show the case where the mask (optimally designed) of the present invention is used, and FIGS. 5A–5I shows the case where no such aperture coding mask is used. In the present example, the EDOF element configured similar to that of FIG. 2B was used. As clearly seen in the figures, a difference in distortions between images of FIGS. 4A–4I and 5A–5I exists due to the aperture coding mask of the present invention.

Figure 6:
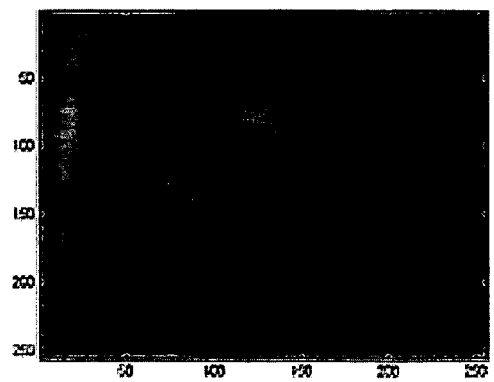
FIG. 6 shows the results of examining the sensitivity of the optical element to wavelength variations.

FIG. 6 shows the results of examining the sensitivity of the coding mask (EDOF element) of the present invention to wavelength variations. In the present example, an imaging lens arrangement (imaging lens with a coding mask) was illuminated with wavelength $\lambda_1=0.8\lambda_0$, wherein $\lambda_0$ is the wavelength for which the mask was designed and fabricated to present pi-phase transition(s), and the defocusing parameter of $4\psi/D^2=0.15$ was used. As could be seen, the out of focus distortion obtained due to the usage of the mask is still very low despite the fact that the mask is no longer optimized (since the mask pattern features are pi-phase transitions for $\lambda_0$ and not for $\lambda_1$).

FIGS. 7A–7D show another experimental results obtained for imaging a Rosette. Here, FIG. 7A shows an image corresponding to the in focus position of the Rosette obtained with no EDOF element of the invention; FIG. 7B shows an in-focus image obtained with the EDOF element; FIG. 7C corresponds to the out of focus position of the Rosette with no EDOF element; and FIG. 7D shows an image of the out of focus Rosette obtained with the EDOF improvement of the present invention. In the present example, the EDOF element configured similar to that of FIG. 2A was used. As shown, the use of the EDOF element of the present invention provides improvement in spatial high frequencies and the effect on the input when the system is in focus.

It should be noted that in all the images presented in FIGS. 4A–4I, 5A–5I, 6 and 7A–7D, showing sufficient extension of the depth of focus, no digital post processing was applied. Applying such processing might further improve the obtained results.

The inventor has performed experimental verification of the extended depth of focus approach for polychromatic spatially non coherent illumination (general lightning). The experimental conditions were as follows: the focal length of the imaging lens F=90 mm, the distance between the imaging lens and the object v=215.9 mm, the distance between the imaging lens and detector (CCD) u=154.3 mm, the aperture of the imaging lens D=16 mm. Thus, the measurement for the phase distortion $\psi$ equals to 13 for the case where the object is moved a distance of 1.5 mm from the in cofus plane, and $\psi=17$ for moving the object a distance of 2 mm. The value of the phase factor $\psi$ is computed following equation 2 above and using the distances and the diameter of the lens (affective aperture of the lens) in the optical system. The experimental results under these conditions are shown in FIGS. 8A–8D and FIGS. 9A–9H. In the present example, the EDOF element configured similar to that of FIG. 2A was used.

Figure 8A:
FIGS. 8A to 8D and FIGS. 9A to 9H show experimental verification of the extended depth of focus technique of the present invention for polychromatic spatially non coherent illumination.
Figure 8B:
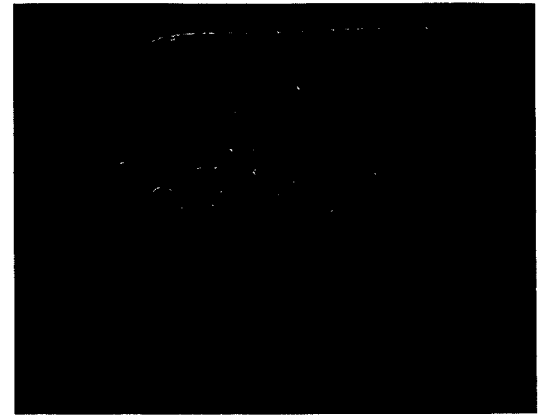
Figure 8C:
Figure 8D:
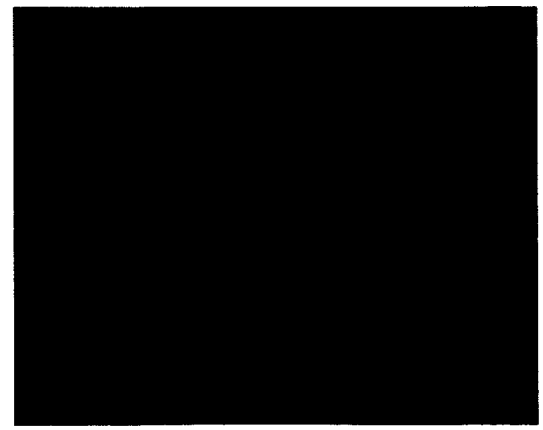

Here, FIG. 8A corresponds to an in-focus position without the use of the optical element of the present invention; FIG. 8B corresponds to the in-focus with such element, FIG. 8C corresponds to the defocused position without the optical element at $\psi=13(+1.5$ mm), and FIG. 8D corresponds to the defocused position with the optical element at $\psi=13(+1.5$ mm).

Figure 9A:
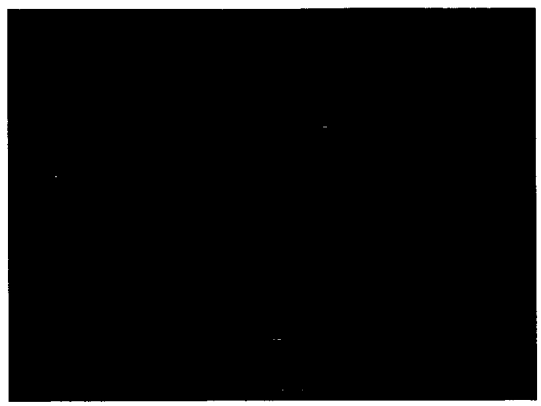
Figure 9B:
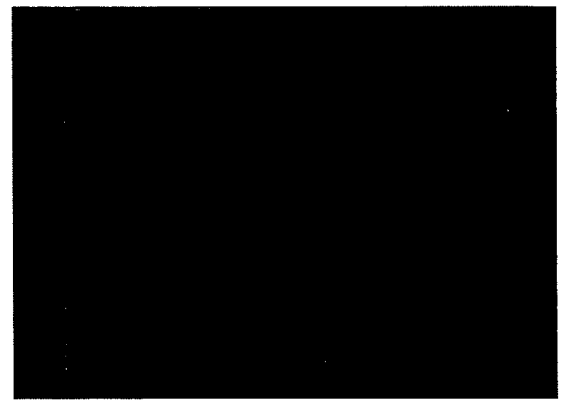
Figure 9C:
Figure 9D:
Figure 9E:
Figure 9F:
Figure 9G:
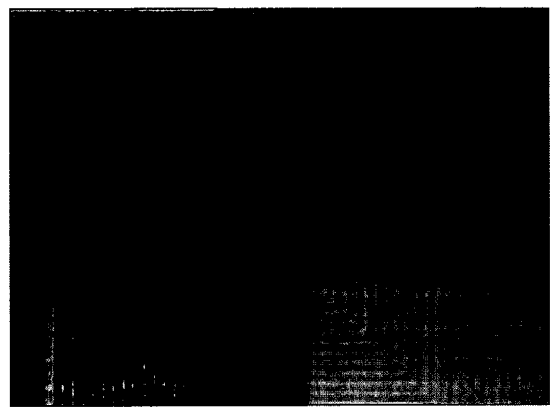
Figure 9H:

FIG. 9A shows an in focus image obtained without the optical element; FIG. 9B shows the defocused image at $\psi=13$ (+1.5 mm) without the element; FIG. 9C shows the defocused image at $\psi=17$ (+2 mm) without the element; FIGS. 9D–9F correspond to FIGS. 9A–9C but with the optical element; FIG. 9G shows the defocused image at $\psi=13(+1.5$ mm) obtained without the element with polychromatic illumination; FIG. 9H shows the defocused image at $\psi=13(+1.5$ mm) obtained with the optical element for polychromatic illumination.

As indicated above, the imaging lens arrangement of the present invention may be used for ophthalmic applications. In order to allow insertion of the imaging lens arrangement into the eye, the surface of the lens arrangement is to be flat. The fabrication techniques suitable to manufacture such an imaging lens arrangement (i.e., flat patterned imaging lens)

include for example etching (wet or dry) or laser drilling or lathe grinding to obtain the desired spatial structure (surface relief), and then filling the evacuated volume by a material of a refraction index different from that of the lens, providing a refraction index difference is such that the outer region of the mask is flat while the desired phase difference is generated, required as buffering phase region that generates proper equalization between regions of the lens aperture for the interference effect. Another realization could be by diffusion or photo polymerization that does not include developing or removing of the polymerized material. Yet another approach which is related to eye surgery could be by implanting artificial tissue having difference in refraction index in comparison to the existing tissue of the eye. The EDOF element of the present invention (having no optical power) is added to the focal power of a certain lens which is to be obtained. For example, if a patient needs −1 diopter glasses and 3 diopters glasses for near and far visions, the EDOF element of the present invention may be appropriately designed to be used on either one of these glasses, being configured in accordance with the respective lens aperture to allow a depth of focus region equivalent to 5 diopters. Actually, in this specific example, a 1 diopter glasses with the EDOF element of the present invention can be used, where the EDOF element is operating around the optical power of the lens (1 diopter) and provides the depth of field region from −1.5 to 3.5 diopters. Hence, the patient may use only one pair of glasses with 1 diopter. This focal power of the glasses (imaging lens) will be added to the EDOF element. Such an EDOF element maximizes the defocused OTF of the lens arrangement (appropriately modulates the CTF profile of the imaging lens of the respective glasses) by generating proper phase interference relation between light portions passing through different regions of the lens, to reduce a quadratic phase factor resulting from light getting out of focus of the imaging lens. The inventor has found that for most patients a common EDOF element configuration can be used, preferably as that of FIG. 2C. Turning back to FIG. 2C, the basic period (of the basic element BE) is about 3 mm, a distance between two adjacent bars is about 1.875 mm, and the bar thickness is about 0.375 mm.

If the EDOF element with its range of depth of focus is used on top of a lens in ophthalmic applications, such as a contact lens, then it may be translated into Diopters range. The diameter of the eye lens (effective aperture of the imaging lens) varies from 2 mm up to 6–7 mm depending on the lightning conditions. The optical element generates a Diopter range within which the image is in focus. The inventor has found that for the resulted range of the phase factor ψ (about up to 17) for lightened environment in which the eye pupil has a diameter of 2 mm, the obtained Diopter range P is more than 5 (from −2.5 up to 2.5). The simulations followed the formula:

$$P = \frac{4\Psi\lambda}{\pi D^2} \quad (6)$$

Figure 10A:
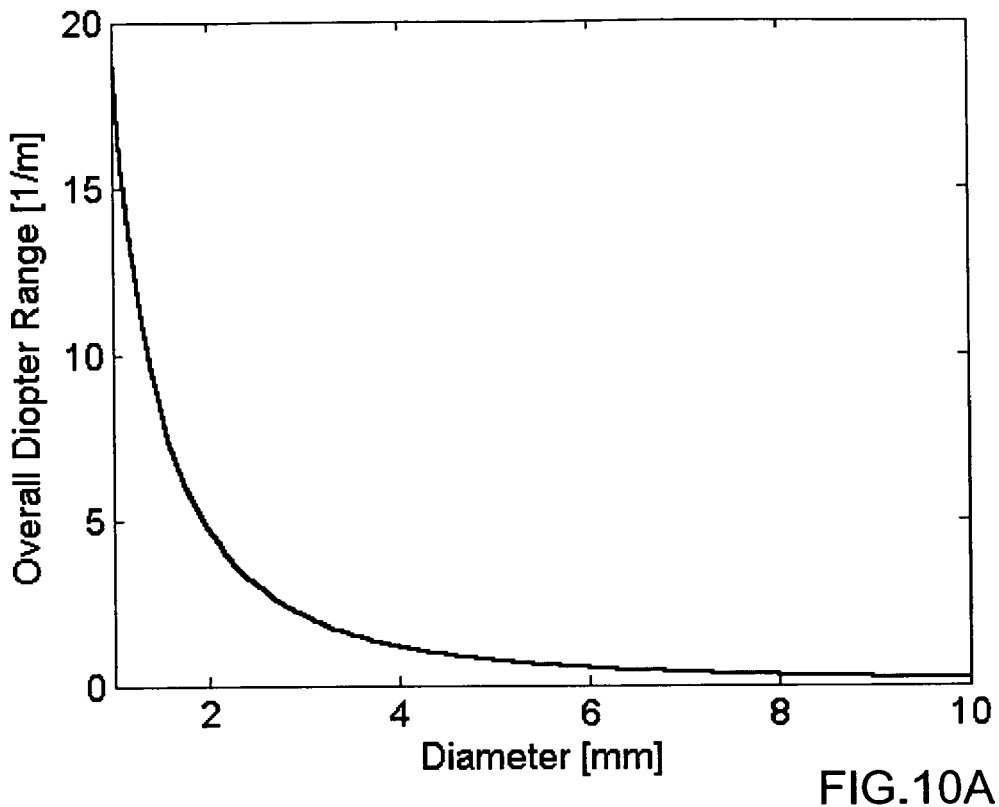
FIG. 10A illustrates the performance of the ophthalmic depth of focus application of the present invention, for the case where the optical element is attached to a contact lens.
Figure 10B:
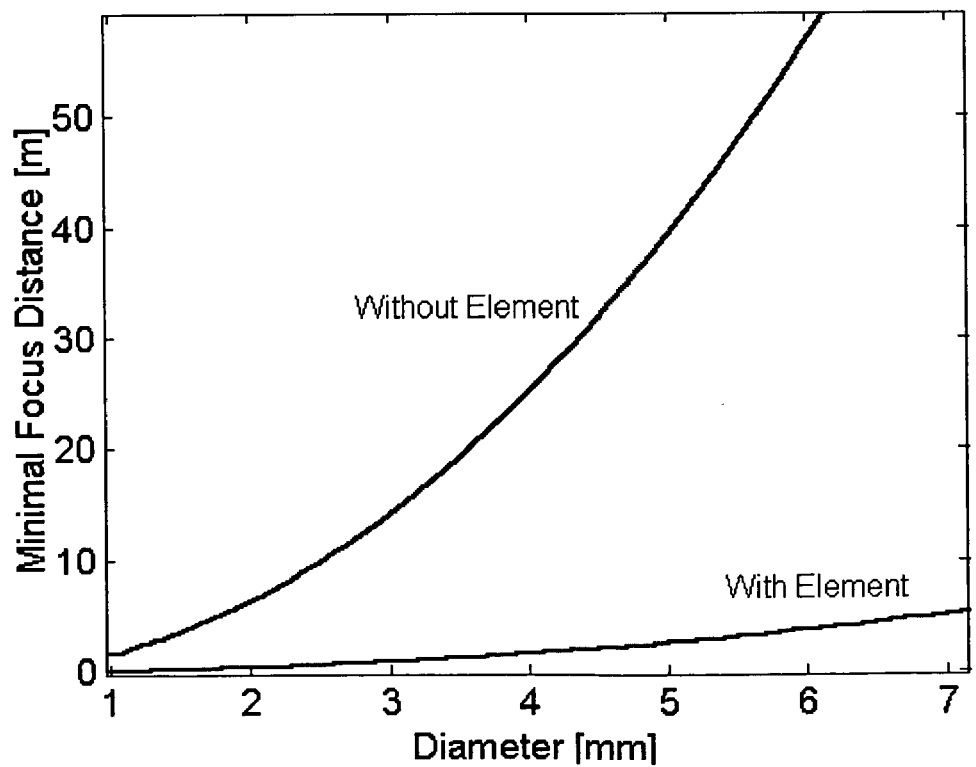
FIG. 10B illustrates the performance of the ophthalmic depth of focus application of the present invention, for the minimal range at which focus is obtained with and without the optical element of the present invention.

FIGS. 10A–10B present the simulation results visualizing the performance of the ophthalmic depth of focus application of the present invention. The simulation of FIG. 10A corresponds to the overall Diopter range obtained due to the fact that the EDOF element is attached to a contact lens. The diameter of the eye lens varies from 2 mm up to 6–7 mm depending on the lightning conditions. The simulations follow Eq. 6 above.

In the simulation of FIG. 10B, an imaging lens with a fixed focal length is used. If the distance between the lens and sensor equals to its focal length (v=F) then the image will be in focus starting from a certain distance, $u_{min}$, up to infinity, wherein the distance $u_{min}$ is determined as:

$$u_{min} = \frac{1}{\frac{4\lambda\Psi}{\pi D^2} + \frac{1}{F} - \frac{1}{v}} = \frac{\pi D^2}{4\lambda\Psi} \quad (7)$$

and for v=F one obtains:

$$u_{min} = \frac{\pi D^2}{4\lambda\Psi} \quad (8)$$

The chart for $u_{min}$ with and without the EDOF element of the present invention is plotted in FIG. 10B. As could be seen, the minimal distance is much smaller when the invented element is in use. Thus, the overall range of focus is much larger. It should be noted that for the human eye, v=15 mm.

The technique of the present invention could be barrier breaking in a vast set of applications including, but not limited to, the following: conventional office devices containing camera such as camcorders, scanners (e.g., barcode scanners) and web cams; conventional imaging systems including camera and detectors, i.e. cellular cameras, car cameras, surveillances cameras, machine vision, photography, HDTV, video conferences, radar imaging systems (that typically suffer from defocus problems), endoscopy and passive bio medical inspections, tomography, etc. The usage of the depth of focus extending element of the present invention in endoscopy and passive biomedical inspections allows for in-body imaging to see organs in focus that otherwise are not, since there is no control on the exact position of the medical apparatus. Some other possible applications of the present invention include correcting chromatic aberrations in various optical systems, for example in optical communication; media reader/writers used with information carriers such as conventional DVD, or multi-layer information carriers utilizing light reflection or fluorescence.

The present invention may also be used in ophthalmic applications as a contact lens, a spectacle lens, an intraocular lens, or any other lens used around or inserted into any part of the eye. An obvious example is the use of the invention for the benefit of short sighted (myopic) people who develop presbyopia, the need for reading glasses as a result of age-related changes in their natural eye lens. In such an application, those people may use a single lens, as a spectacle lens, contact lens, intracorneal lens, phakic intraocular lens or aphakic intraocular lens, or a lens inserted elsewhere in the eye. In this fashion, they will use one lens for seeing at any distance, near or far. Another obvious utilization of the invention is in an intraocular lens, the artificial lens implanted in the eye after removal of a cataract. Currently, the regular artificial lens have only a single focus and thus the person into whose eye the lens was implanted has a very limited depth of focus and have to use spectacles for most distances of regard. Incorporation of the invention into the implanted lens will afford the patient focused vision at all distances. Another example of ophthalmic use is as a replacement of multifocal (progressive) spectacle lens, which are conventionally designed such that every segment of the lens surface has a different focus and thus the patient has to move his eyes to focus on objects at different distances. Incorporation of the invention into a spectacle or contact lens will enable the presbyopic wearer to see in focus objects at all distances through any part of the lens.

In all the applications of the invention, including the examples above, the image from objects at different distances are focused on the retina (or sensor) without appreciable loss of energy, in contradistinction to the situation in multifocal contact or intraocular lenses.

Those skilled in the art will readily appreciate that various modifications and changes can be applied to the embodiments of the invention described hereinbefore without departing from its scope defined in and by the appended claims.

I claim:

1. An imaging arrangement comprising: an imaging lens having a certain affective aperture, and an optical element associated with said imaging lens and configured to provide an extended depth of focus of the imaging arrangement, said optical element being configured as a phase-affecting, non-diffractive optical element defining a spatially low frequency phase transition, said optical element together with the imaging lens defining a predetermined pattern formed by spaced-apart optically transparent features of different optical properties, position of at least one phase transition region of the optical element within the imaging lens plane being determined by at least a dimension of said affective aperture.

2. The arrangement of claim 1, wherein said optical element is configured as a phase-only element.

3. The arrangement of claim 2, wherein said optical element is configured as a binary mask.

4. The arrangement of claim 1, wherein said optical element is a configured as a phase and amplitude affecting element.

5. The arrangement of claim 1, wherein the optical element is configured to maximize a defocused optical transfer function (OTF) of the imaging arrangement by providing the out of focus OTF as much as possible away from zero.

6. The arrangement of claim 5, wherein the optical element is configured to produce proper phase interference relation between light portions passing through different regions of the imaging arrangement corresponding to the different features of the pattern to thereby reduce a quadratic phase factor resulting from light getting out of focus of the imaging lens.

7. The arrangement of claim 1, wherein said at least one transition region is configured as a pi-phase transition for a certain wavelength for which the optical element is designed.

8. The arrangement of claim 1, wherein the position of said at least one transition region with respect to the imaging lens is determined by optical power of the imaging lens.

9. The arrangement of claim 5, wherein the position for N transition regions of the optical element within the imaging lens plane maximizing the OTF is determined as:

$$\max_{a_n}\left\{\min\left\{\left[\tilde{D}(v)\sum_{n=1}^{N}a_n\mathrm{rect}\left(\frac{v-n\Delta v}{\Delta v}\right)\right]\otimes\left[\tilde{D}(v)\sum_{n=1}^{N}a_n\mathrm{rect}\left(\frac{v-n\Delta v}{\Delta v}\right)\right]\right\}\right\}$$

values for $a_n$ providing maximum for minima of an expression for auto correlation of a Coherent Transfer Function (CTF) of the imaging lens, where $a_n$ equals either 1 or −1, $\tilde{D}(v)$ being the CTF of the imaging lens corresponding to out of focus position of an object being imaged and being determined as $$\tilde{D}(v)=\exp\left(\frac{i4\Psi v^2}{D^2}\right),$$

wherein D is the affective aperture dimension, v is a coordinate of the affective aperture in the CTF plane, and ψ is a phase factor representing a degree of getting out of focus.

10. The arrangement of claim 1, wherein said at least one transition region has a sub-pattern formed by an array of variable phase transition sub-regions.

11. The arrangement of claim 7, wherein said at least one pi-phase transition region has a sub-pattern formed by an array of variable pi-phase transition sub-regions.

12. The arrangement of claim 1, wherein the optical element is configured as at least one annular transition region.

13. The arrangement of claim 1, wherein the optical element is configured as a grid.

14. The arrangement of claim 1, wherein said optical element is spaced-apart from the imaging lens along an optical axis of the imaging lens.

15. The arrangement of claim 1, wherein said optical element is attached to the imaging lens.

16. The arrangement of claim 1, wherein said optical element is made integral with the imaging lens.

17. The arrangement of claim 1, wherein said optical element is configured as a mask formed by an array of said transition regions arranged in a spaced-apart relationship being spaced by the optically transparent regions of the imaging lens within the imaging lens plane.

18. The arrangement of claim 16, wherein said at least one transition region is formed as a surface relief on the imaging lens surface, defining a lens thickness within said at least one region different from that within other regions of the lens.

19. The arrangement of claim 16, wherein said optical element is configured as a mask formed by an array of the phase transition regions arranged in a spaced-apart relationship spaced by the optically transparent regions of the imaging lens.

20. The arrangement of claim 16, wherein said at least one transition region is formed by a material having refractive index different from that of the imaging lens material.

21. The arrangement of claim 16, wherein said optical element is configured as a mask formed by an array of the phase transition regions formed by a material having refractive index different from that of the imaging lens material.

22. The arrangement of claim 5, wherein the optical element is configured to maximize the OTF by reducing high-frequency cancellation at large shifts of a Coherent Transfer Function (CTF) of the imaging lens.

23. The arrangement of claim 5, wherein the optical element is configured to maximize the OTF by reducing sensitivity of the lens arrangement to shifts of a Coherent Transfer Function (CTF) of the imaging lens while getting out of focus.

24. The arrangement of claim 23, wherein the optical element is configured to produce periodic replication of a lateral phase shape of a light field propagating through the imaging lens.

25. The arrangement of claim 23, wherein the optical element is configured in accordance with a free space propagation of the optical element function for a distance between the optical element and the imaging lens plane.

26. An imaging arrangement comprising: an imaging lens having a certain affective aperture, and an optical element associated with said imaging lens and configured to provide an extended depth of focus of the imaging arrangement, said optical element being configured as a phase-only, non-diffractive binary mask defining a spatially low frequency phase transition, said optical element together with the imaging lens defining a predetermined pattern formed by spaced-apart optically transparent features of different optical properties, position of at least one phase transition region of the optical element within the imaging lens plane being determined by at least a dimension of said affective aperture.

27. An imaging arrangement comprising: an imaging lens having a certain affective aperture, and an optical element associated with said imaging lens and configured to provide an extended depth of focus of the imaging arrangement, said optical element being configured as a phase-affecting, non-diffractive optical element defining a spatially low frequency phase transition, said optical element together with the imaging lens defining a predetermined pattern formed by spaced-apart optically transparent features of different optical properties, position of at least one phase transition region of the optical element within the imaging lens plane being determined by at least a dimension of said affective aperture such that the optical element produces proper phase interference relation between light portions passing through different regions of the imaging arrangement corresponding to the different features of the pattern to thereby reduce a quadratic phase factor resulting from light getting out of focus of the imaging lens and maximize a defocused optical transfer function (OTF) of the imaging lens arrangement by providing the out of focus OTF as much as possible away from zero.

28. An imaging arrangement comprising an imaging lens having a certain affective aperture, and an optical element associated with said imaging lens and configured to provide an extended depth of focus of the imaging arrangement, said optical element being configured as a phase-affecting, non-diffractive element defining a certain pattern of spatially low frequency phase transitions within a plane of the imaging lens, such that said optical element together with the imaging lens determine a predetermined pattern formed by spaced-apart optically transparent features differently affecting phase of light passing through the imaging arrangement, positions of the phase transitions of the optical element within the imaging lens plane being determined by at least a dimension of said affective aperture to reduce sensitivity of the imaging arrangement to shifts of a Coherent Transfer Function (CTF) of the imaging lens while getting out of focus.

29. An imaging arrangement for creating an image of an object on a detector plane, the system comprising an imaging lens arrangement formed by an imaging lens having a certain affective aperture and an optical element configured to provide an extended depth of focus of the imaging arrangement, said optical element being configured as a phase-affecting, non-diffractive element defining a spatially low frequency phase transition, said optical element together with the imaging lens defining a predetermined pattern formed by spaced-apart optically transparent features of different optical properties, position of at least one phase transition region of the optical element within the imaging lens plane being determined by at least a dimension of said affective aperture such that the optical element produces proper phase interference relation between light portions passing through different regions of the imaging arrangement corresponding to the different features of the pattern to thereby enable reducing a quadratic phase factor resulting from light getting out of focus of the imaging lens and maximize a defocused optical transfer function (OTF) of the imaging arrangement.

30. An optical element for use with an imaging lens for extending depth of focus of imaging, the optical element being configured as a phase-affecting, non-diffractive optical element defining a predetermined pattern of spatially low frequency phase transitions, said pattern being defined by an affective aperture of the given imaging lens.

31. An optical element for use with an imaging lens for extending depth of focus of imaging, the optical element being configured as a phase-only, non-diffractive binary element defining a predetermined pattern of spatially low frequency phase transitions, said pattern being defined by an affective aperture of the given imaging lens.

32. An optical element for extending depth of focus of imaging, the optical element being configured as a phase-affecting, non-diffractive optical element defining a spatially low frequency phase transition, the optical element defining a predetermined pattern of phase transition regions, said transition regions being arranged in accordance with an affective aperture of a given imaging lens for which the optical element is designed, so as to provide said transition regions of the optical element within predetermined positions in the imaging lens plane, to provide periodic replication of a lateral phase shape of a light field propagating through the imaging lens with said optical element.

33. An optical element for extending depth of focus of imaging, the optical element being configured as a phase-only, non-diffractive binary element defining a spatially low frequency phase transition, the optical element defining a predetermined pattern of phase transition regions, said transition regions being arranged in accordance with an affective aperture of a given imaging lens for which the optical element is designed, so as to provide said transition regions of the optical element within predetermined positions in the imaging lens plane, to provide periodic replication of a lateral phase shape of a light field propagating through the imaging lens with said optical element.

34. A method for providing a certain extended depth of focus of an imaging system, the method comprising applying an aperture coding to an imaging lens having a certain effective aperture, by applying to the imaging lens a phase-affecting non-diffractive optical element configured to define a spatially low frequency phase transition arrangement and thereby provide a predetermined pattern of spaced-apart substantially optically transparent features of different optical properties within the imaging lens plane, thereby producing phase interference relation between light portions passing through different regions of the lens arrangement corresponding to the different features of the pattern so as to reduce a quadratic phase factor resulting from light getting out of focus of the imaging lens and maximize a defocused optical transfer function (OTF) of the imaging lens arrangement.

35. A method for providing a certain extended depth of focus of an imaging system, the method comprising designing a phase-affecting non-diffractive optical element to be used with an imaging lens having a certain effective aperture, said designing comprising selecting N positions for phase transitions within the imaging lens effective aperture as those providing maximal contrast of an Optical Transfer Function (OTF) of the imaging system under a set of out of focus locations, thereby providing the out of focus OTF as much as possible away from zero.

36. The method of claim 35, wherein the positions for said N transition regions of the optical element within the imaging lens plane maximizing the OTF are determined as:

$$\max_{a_n}\left\{\min\left\{\left[\tilde{D}(v)\sum_{n=1}^{N}a_n\text{rect}\left(\frac{v-n\Delta v}{\Delta v}\right)\right]\otimes\left[\tilde{D}(v)\sum_{n=1}^{N}a_n\text{rect}\left(\frac{v-n\Delta v}{\Delta v}\right)\right]\right\}\right\}$$

values for $a_n$ providing maximum for minima of an expression for auto correlation of a Coherent Transfer Function (CTF) of the imaging lens, where $a_n$ equals either 1 or –1, $\tilde{D}(v)$ being the CTF of the imaging lens corresponding to out of focus position of an object being imaged and being determined as $$\tilde{D}(v)=\exp\left(\frac{i4\Psi v^2}{D^2}\right),$$

wherein D is the affective aperture dimension, v is a coordinate of the affective aperture in the CTF plane, and, and $\psi$ is a phase factor representing a degree of getting out of focus.

37. The method of claim 35, comprising fabricating a mask formed by an arrangement of the N transitions spaced-apart from each other in accordance with said selected N positions.

38. The method of claim 37, comprising attaching said mask to the surface of the imaging lens aperture.

39. The method of claim 35, comprising patterning the surface of the imaging lens aperture to form a mask of the N transitions spaced-apart from each other in accordance with said selected N positions.

40. The method of claim 38, comprising providing said surface substantially flat to thereby allow insertion of the patterned imaging lens into a patient's eye.

41. The method of claim 39, comprising providing said surface substantially flat to thereby allow insertion of the patterned imaging lens into a patient's eye.

42. The method of claim 35, wherein the designing of the optical element comprises producing a phase interference relation between light portions passing through said N regions and spaces between them to thereby reduce a quadratic phase factor resulting from light getting out of focus of the imaging lens and maximize a defocused optical transfer function (OTF) of an arrangement formed by the imaging lens and the optical element.

43. The method of claim 39, wherein said patterning comprises applying material removal to the lens regions within said N positions, and filling said regions, from which the lens material has been removed, by a material of a refraction index different from that of the lens, so as to provide a refraction index difference such that the outer region of the patterned lens is flat and proper equalization between the different material regions is provided to produce a phase interference relation between light portions passing through different material regions to thereby reduce a quadratic phase factor resulting from light getting out of focus of the imaging lens and maximize a defocused optical transfer function (OTF) of the patterned imaging lens.

44. The method of claim 39, wherein said patterning comprises applying diffusion or photo polymerization to the lens regions within said N positions, so as to provide a refraction index difference between said N regions and spaces between them such that the outer region of the patterned lens is flat and proper equalization between the different material regions is provided to produce a phase interference relation between light portions passing through different material regions to thereby reduce a quadratic phase factor resulting from light getting out of focus of the imaging lens and maximize a defocused optical transfer function (OTF) of the patterned imaging lens.

45. The method of claim 35, comprising implanting in the patient's eye tissue, within said selected M positions, an artificial tissue having a refraction index different from that of the eye tissue.

* * * * *